US011007309B2

(12) United States Patent
Carpani et al.

(10) Patent No.: US 11,007,309 B2
(45) Date of Patent: *May 18, 2021

(54) EXTRACORPOREAL BLOOD TREATMENT APPARATUS AND METHOD OF SETTING AN EXTRACORPOREAL BLOOD TREATMENT

(71) Applicant: GAMBRO LUNDIA AB, Lund (SE)

(72) Inventors: Michela Carpani, San Biagio (IT); Guy Mercier, Bron (FR); David Nepote-Vesino, Jonage (FR)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/522,016

(22) Filed: Jul. 25, 2019

(65) Prior Publication Data

US 2019/0344003 A1 Nov. 14, 2019

Related U.S. Application Data

(63) Continuation of application No. 14/431,535, filed as application No. PCT/IB2013/058927 on Sep. 27, 2013, now Pat. No. 10,391,218.

(Continued)

(30) Foreign Application Priority Data

Sep. 28, 2012 (EP) .................................. 12006802

(51) Int. Cl.
*A61M 1/16* (2006.01)
*A61M 1/34* (2006.01)
*A61M 1/36* (2006.01)

(52) U.S. Cl.
CPC ............ *A61M 1/1603* (2014.02); *A61M 1/16* (2013.01); *A61M 1/1613* (2014.02);

(Continued)

(58) Field of Classification Search
CPC .............. A61M 1/1603; A61M 1/1613; A61M 1/3403; A61M 1/341; A61M 1/3441; A61M 2205/52

See application file for complete search history.

(56) References Cited

U.S. PATENT DOCUMENTS 4,381,999 A 5/1983 Boucher
4,735,727 A 4/1988 Heitmeier
(Continued)

FOREIGN PATENT DOCUMENTS

DE 29902953 U1 7/2000
DE 29902953 U 8/2000
(Continued)

OTHER PUBLICATIONS

Sequential PUF Dialysis Treatment.pdf—Jul. 7, 2010—akstubel, (https://youtu.be/aVyY9v-VS64).

(Continued)

*Primary Examiner* — Bradley R Spies
(74) *Attorney, Agent, or Firm* — Mueting Raasch Group (57) ABSTRACT

It is described an extracorporeal blood treatment apparatus (1) with a user interface (12) device capable configuring and allowing execution of one or more isolated ultrafiltration tasks during the course of a dialysis treatment. The extracorporeal blood treatment apparatus (1) is controlled in a normal mode, where dialysis fluid is fed to the blood treatment unit (2), and in an isolated ultrafiltration mode, where fresh dialysis fluid is no longer fed to the blood treatment unit (2).

20 Claims, 7 Drawing Sheets

Related U.S. Application Data (60) Provisional application No. 61/706,886, filed on Sep. 28, 2012.

(52) U.S. Cl.
CPC .......... *A61M 1/341* (2014.02); *A61M 1/3403* (2014.02); *A61M 1/3406* (2014.02); *A61M 1/3413* (2013.01); *A61M 1/3434* (2014.02); *A61M 1/3437* (2014.02); *A61M 1/3441* (2013.01); *A61M 1/1601* (2014.02); *A61M 1/165* (2014.02); *A61M 1/3431* (2014.02); *A61M 1/3626* (2013.01); *A61M 2205/3334* (2013.01); *A61M 2205/3393* (2013.01); *A61M 2205/505* (2013.01); *A61M 2205/52* (2013.01)

(56) References Cited

U.S. PATENT DOCUMENTS

| | | | |
|---|---|---|---|
| 5,247,434 | A | 9/1993 | Peterson |
| 5,326,476 | A | 7/1994 | Grogan |
| 5,580,460 | A | 12/1996 | Polaschegg |
| 6,284,141 | B1 | 9/2001 | Shaldon |
| 6,423,022 | B1 | 7/2002 | Roecher |
| 6,726,647 | B1 | 4/2004 | Sternby |
| 6,830,693 | B2 | 12/2004 | Govoni |
| 6,881,344 | B2 | 4/2005 | Vasta |
| 2005/0045540 | A1 | 3/2005 | Connell |
| 2005/0274658 | A1 | 12/2005 | Rosenbaum |
| 2007/0138069 | A1 | 6/2007 | Roncadi et al. |
| 2011/0163034 | A1 | 7/2011 | Castellarnau |
| 2011/0284464 | A1 | 11/2011 | Roncadi |

FOREIGN PATENT DOCUMENTS

| | | |
|---|---|---|
| EP | 0686404 A1 | 12/1995 |
| EP | 1698360 A1 | 9/2006 |
| EP | 1698360 B1 | 9/2006 |
| EP | 2163272 A1 | 3/2010 |
| WO | WO 97/44072 | 11/1997 |
| WO | WO 2007/072116 | 6/2007 |

OTHER PUBLICATIONS

Fresenius 5008 procedures.pdf—Sep. 2012—Manitoba Renal Program.
Brief Instructions Standard Dialysis (Braun).pdf—Braun—Aug. 2008.
Dialog+ Dialysis Machine (Braun 2).pdf—Braun—May 2010.
PCT/IB2013/058927 International Search Report and Written Opinion dated May 22, 2014 (17 pages).

EXTRACORPOREAL BLOOD TREATMENT APPARATUS AND METHOD OF SETTING AN EXTRACORPOREAL BLOOD TREATMENT

This application is a continuation application of U.S. application Ser. No. 14/431,535 filed Mar. 26, 2015, which is a U.S. National Stage Application of International Application No. PCT/IB2013/058927, filed Sep. 27, 2013, which was published in English on Apr. 3, 2014 as International Patent Publication WO 2014/049560 A2, which claims the benefit under 35 U.S.C. 119(e) of U.S. Provisional Application No. 61/706,886 filed Sep. 28, 2012. International Application No. PCT/IB2013/058927 also claims priority to European Application No. 12006802.8 filed Sep. 28, 2012. A certified copy of European Application No. 12006802.8 filed Sep. 28, 2012, was provided in, and is available in, U.S. patent application Ser. No. 14/431,535 for which certified copy is available in PAIR.

The invention relates to an extracorporeal blood treatment apparatus with improved set up and control capabilities; the extracorporeal blood treatment apparatus may be—without limitation—a hemodialysis or hemodiafiltration apparatus. The invention also concerns a method for setting and controlling during treatment an extracorporeal blood treatment apparatus.

In a haemodialysis treatment a patient's blood and a treatment liquid approximately isotonic with blood flow are circulated in a dialysate compartment of a treatment unit—e.g. a hemodialyzer—while blood is circulated in the blood compartment of the same hemodialyzer. The two compartments are separated by a semipermeable membrane so that impurities and undesired substances present in the blood (urea, creatinine, etc.) may migrate by diffusive transfer from the blood into the treatment liquid. The ion concentration of the treatment liquid is chosen so as to correct the ion concentration of the patient's blood. In a treatment by haemodiafiltration, a convective transfer by ultrafiltration, resulting from a positive pressure difference created between the blood side and the treatment-liquid side of the membrane of an hemodiafilter, is added to the diffusive transfer obtained by dialysis.

Various solutions are known for setting an ultrafiltration profile before the treatment start such that the blood treatment apparatus may then be controlled to follow in course of the treatment time the set ultrafiltration.

For instance, U.S. Pat. No. 5,247,434 shows a method of programming a time-varying parameter by touching a touch screen at a plurality of points to define points on a parameter-versus-time curve Document U.S. Pat. No. 5,326,476 teaches a further method for entering a time variable parameter, ultrafiltration in particular, in a hemodialysis machine, having a programmable memory and having ultrafiltration capability, so as to enable the machine to perform ultrafiltration of fluid from a patient according to a time-variable ultrafiltration profile. The method disclosed in U.S. Pat. No. 5,326,476 comprises the following steps:
(a) entering into the programmable memory a prescribed time for dialysis;
(b) entering into the programmable memory a target ultrafiltration volume of fluid to be removed from the patient;
(c) entering into the programmable memory a proposed ultrafiltration profile being representable as a plot of coordinates on an ultrafiltration rate axis and a time axis and defining a profile ultrafiltration volume; and
(d) shifting the proposed ultrafiltration profile along the ultrafiltration rate axis to the degree necessary to make the profile ultrafiltration volume equal to the target ultrafiltration volume, so as to allow the hemodialysis machine to achieve, while ultrafiltrating the fluid according to the shifted ultrafiltration profile, the entered target ultrafiltration volume within the entered prescribed time.

A further known technique is described in U.S. Pat. No. 6,830,693, which relates to a method of setting up a dialysis treatment in a dialysis machine comprising the steps of: determining conditions of a dialysis treatment adapted to a specific patient; determining a first function (U(t)) of a first quantity (U) characterizing the dialysis treatment as a function of time (t), the first function (U(t)) satisfying said conditions of the dialysis treatment and corresponding to a curve having a defined shape; and determining a second function (C(t)) of a second quantity (C) characterizing the dialysis treatment, the second function (C(t)) being correlated with the first function (U(t)) by constants (M, N) determined experimentally and the second function (C(t)) corresponding to a curve having a shape of the same kind as the shape of the first curve.

Furthermore, US reference U.S. Pat. No. 6,881,344 relates to a user interface and to a method of setting up a dialysis treatment in a dialysis machine wherein a group of parametric functions (U(t, P); C(t, P)) representing ultrafiltration or conductivity as a function of time (t) and of a parameter (P) are provided. By imposing boundary conditions that are characteristic of a particular therapy and assigning values to the parameter (P) the user selects the curve and the machine calculates and displays the curves corresponding to the user's selection; the user can then confirm selection on the basis of the images of the curves.

Finally, US2011/0284464 shows a blood treatment apparatus with a user interface designed for setting up a time-varying parameter such as ultrafiltration.

Although the above solutions may have been adopted in the past, it is of interest to be able to easily set up and run a blood treatment apparatus such that portions of the treatment are conducted without circulation of treatment liquid in the dialysate chamber of the treatment unit. In such condition, the apparatus exclusively actuates a convective transfer by ultrafiltration (herein referred to as 'isolated ultrafiltration') through the semipermeable membrane of the hemodialyzer or hemodiafilter.

It is therefore an object of the present invention to provide an apparatus and a method adapted to be implemented in a blood treatment apparatus for the convenient setting of a treatment procedure comprising intervals during which the apparatus is requested to perform isolated UF.

Moreover, it is an auxiliary object providing an apparatus and a method for setting either before treatment start or in the course of the treatment, as many time as needed, one or more intervals during which the apparatus is requested to perform isolated UF.

Additionally, it is another auxiliary object providing solutions which can be implemented with minimal changes to conventional blood treatment apparatus.

Another auxiliary object is an improved blood treatment apparatus implementing the innovative aspects of the invention without impairing on operating reliability and without causing risks to the patient under treatment.

SUMMARY

At least one of the above objects is substantially reached by an apparatus according to one or more of the appended claims.

Apparatus and methods according to aspects of the invention and capable of achieving one or more of the above objects are here below described.

DETAILED DESCRIPTION

Figure 2:
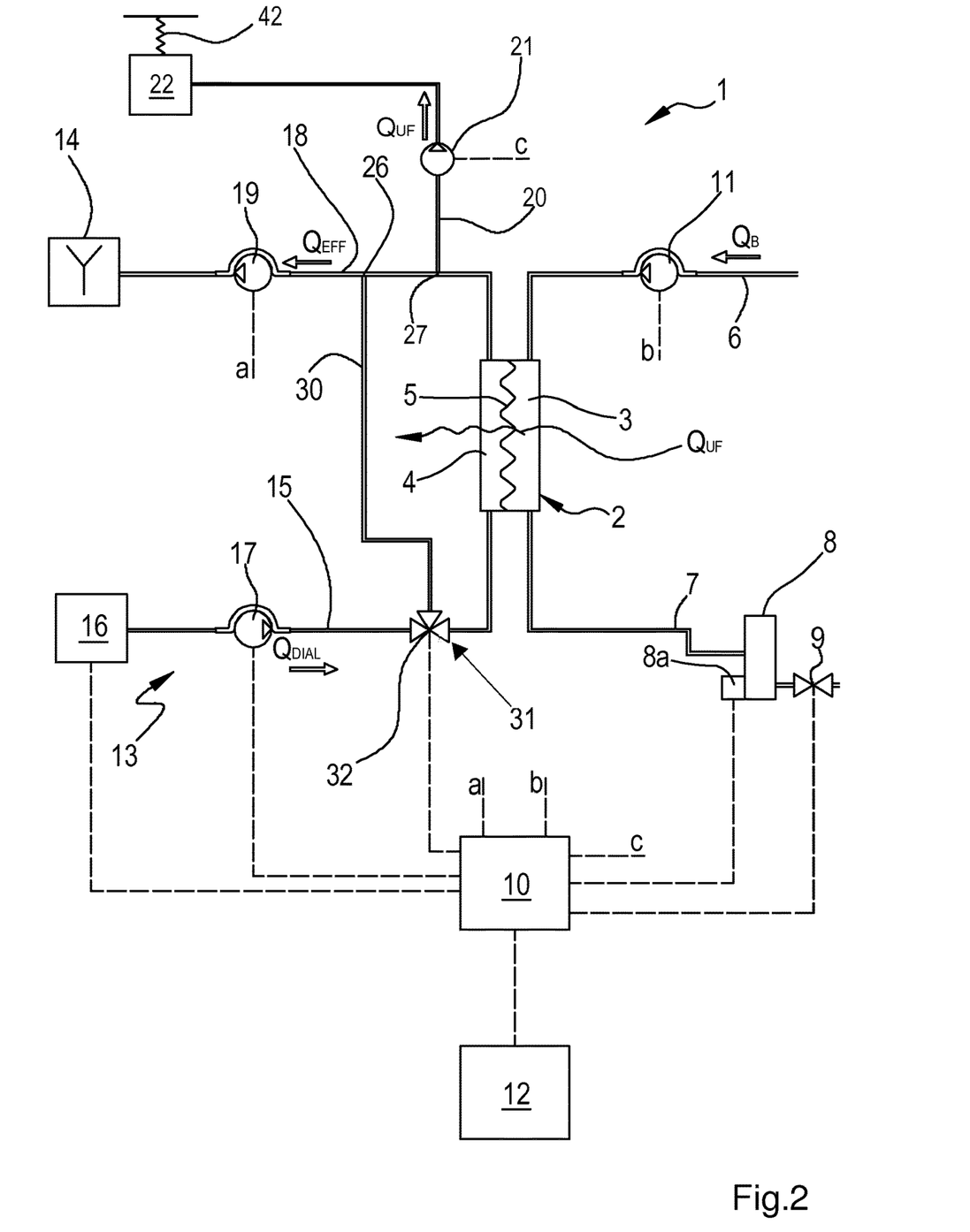
FIG. 2 shows a schematic diagram of an alternative embodiment of a blood treatment apparatus according to another aspect of the invention.
Figure 3:
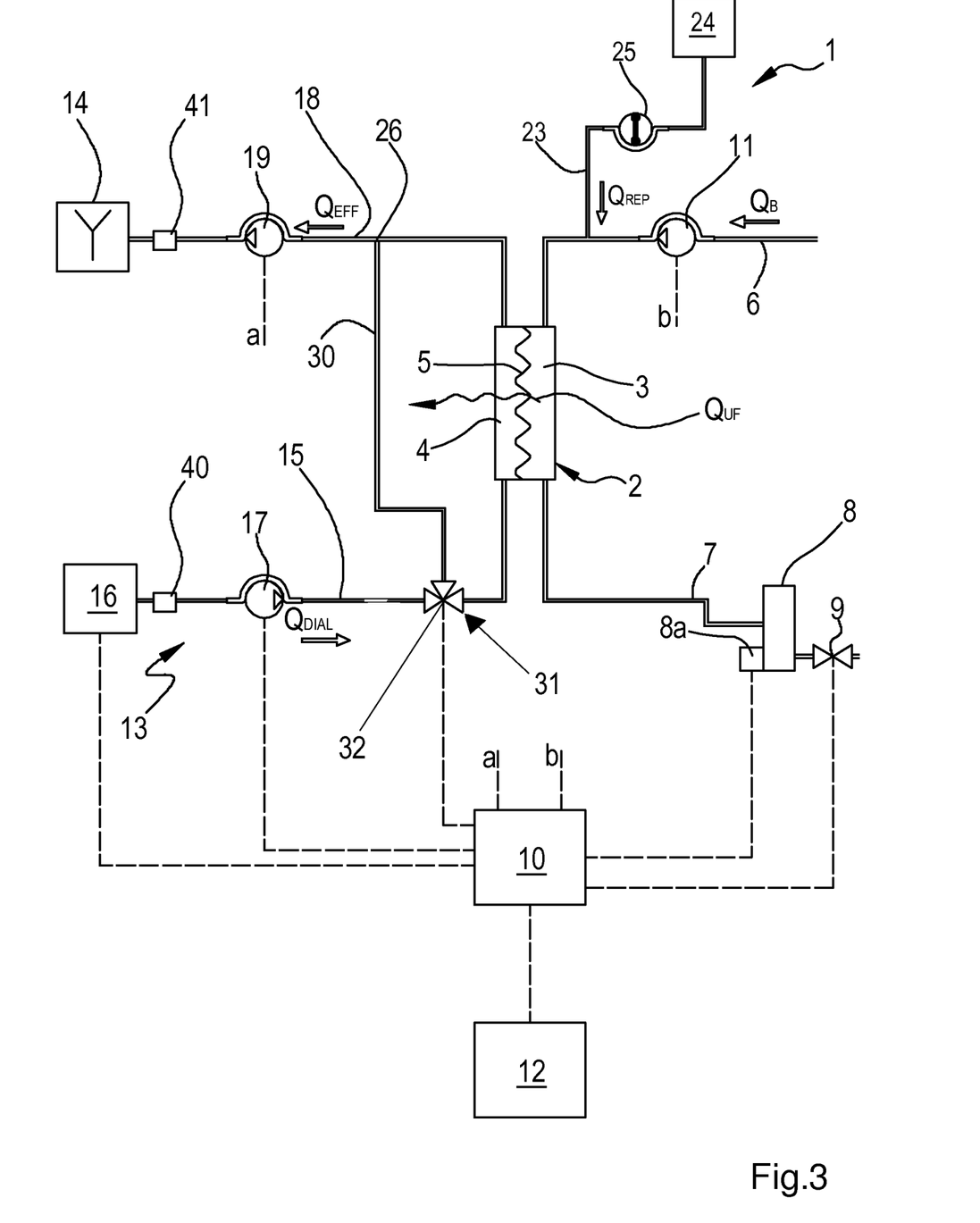
FIG. 3, shows a schematic diagram of a further embodiment of a blood treatment apparatus according to another aspect of the invention.

The present invention relates to a new method for setting up and controlling an extracorporeal blood treatment apparatus, as well as to extracorporeal blood treatment apparatus implementing said device and method. It should be noted that the innovative aspects of the invention may be implemented in any type of extracorporeal blood treatment apparatus of the type using a semipermeable membrane blood treatment unit and having a fresh treatment fluid line connected to a secondary chamber of the blood treatment unit. In the present description, the innovative aspects of the invention are described with reference to an hemodialysis blood treatment apparatus, which is schematically represented in the examples of FIGS. 1 and 2, and with reference to an hemodiafiltration blood treatment apparatus, which is schematically represented in the example of FIG. 3.

In below description and in FIGS. 1, 2 and 3 same components are identified by same reference numerals.

Figure 1:
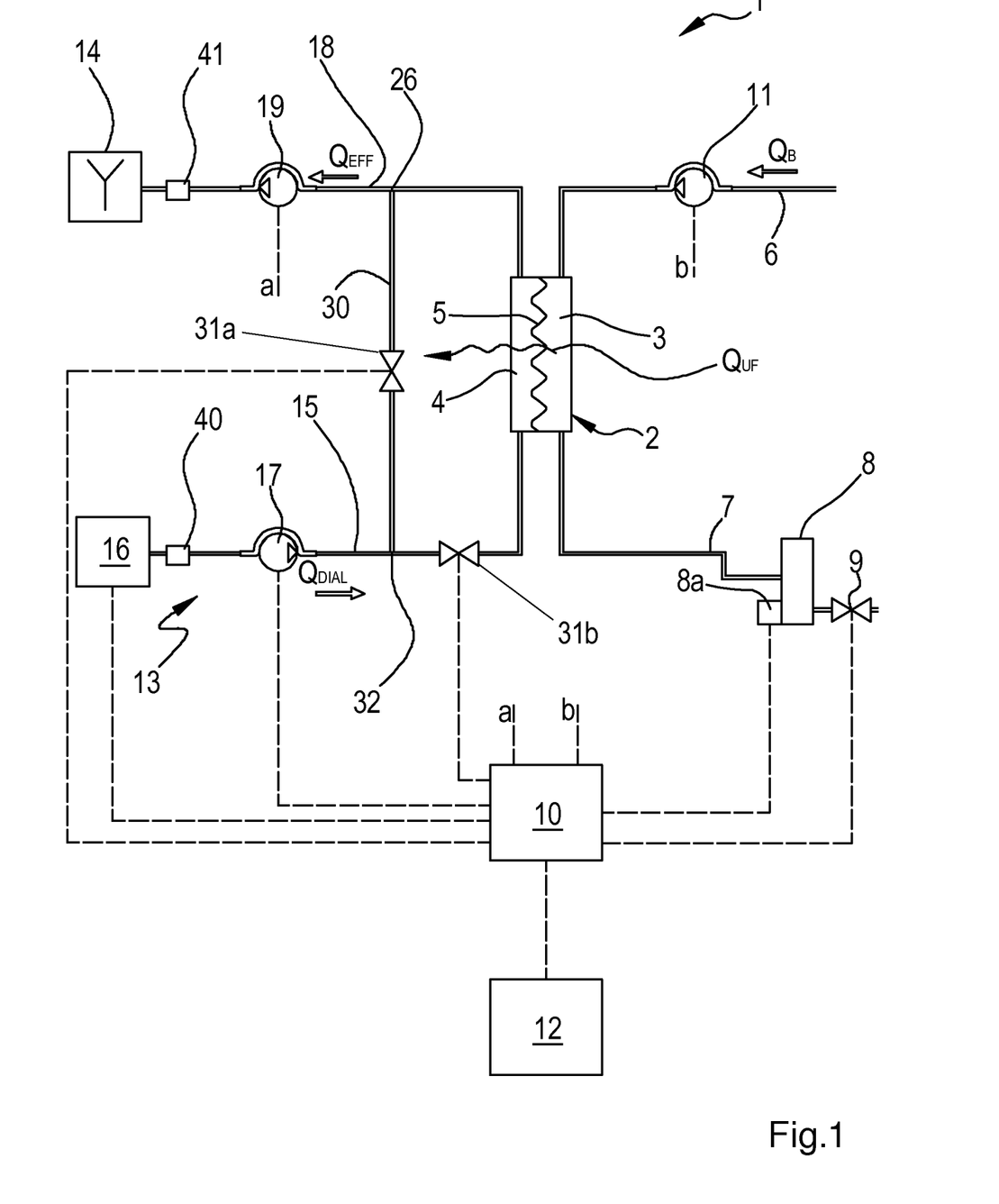
FIG. 1 shows a schematic diagram of a blood treatment apparatus according to one aspect of the invention.

FIG. 1 shows an apparatus 1 having a treatment unit 2 presenting a primary chamber 3 and a secondary chamber 4 separated by a semi-permeable membrane 5, for instance comprising a set of hollow fibers or a set of flat membranes; depending upon the specific treatment to be delivered to the patient, the membrane of unit 2 may be selected to have different properties and performances. A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. An air separator, such as a bubble trap 8 may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles having size above certain safety threshold(s) are detected. As shown in FIG. 1, the blood flow through the blood lines is regulated by a blood pump 11, for instance a peristaltic blood pump, acting either on the blood withdrawal line (as shown in FIG. 1) or on the blood return line (not shown) and controlled by control unit 10. Although this is not shown in the attached drawings, two blood pumps may be used: one acting on the blood withdrawal line and one on the blood return line.

The apparatus 1 comprises a hydraulic circuit 13 which is responsible for feeding fresh treatment fluid (e.g. dialysis fluid) to the secondary chamber 4 and for withdrawing and discharging to a waste 14 the spent treatment liquid exiting from the secondary chamber. The hydraulic circuit includes a fresh fluid line 15 which has a first end connected to a source 16 of fresh treatment fluid and a second end connected to the inlet of the secondary chamber 4. The source of fresh treatment liquid may be an online fluid preparation section or a container, such as a bag, hosting a prefixed quantity of pre-manufactured fluid. Note that the design of the online fluid preparation section is not relevant for the purpose of the present invention and is therefore not described in detail: for instance the online preparation section may include at least one connector to a water inlet, one or more filtering units, one or more lines for supplying concentrates, and optionally one or more units for heating and degassing the fluid under preparation. Irrespective of the type of source 16, the hydraulic circuit 13 comprises a dialysis fluid pump 17 working on the fresh fluid line 15 under the control of said control unit 10, to supply fluid to the secondary chamber at a flow rate $Q_{DIAL}$. The hydraulic circuit also includes a spent fluid line 18 which is connected, at a first end, to an outlet of the secondary chamber 4 and, at its second end, to the waste 14 which, for example, may be a discharge conduit or an effluent fluid container collecting all or part of the fluid extracted from the secondary chamber. A spent fluid pump 19 operates on the spent fluid line under the control of control unit 10 to regulate the flow rate $Q_{EFF}$ across the spent fluid line. As shown in FIG. 2, the apparatus may also include an ultrafiltration line 20 branching off the spent fluid line 18 (at branch off point 27) and provided with a respective ultrafiltration pump 21 also controlled by control unit 10. In case, as for the example of FIG. 1, the hydraulic circuit 13 does not have a dedicated ultrafiltration line, the spent treatment fluid and ultrafiltered fluid crossing the membrane 5 (note the ultrafiltration rate is represented by $Q_{UF}$ in the figures) are both conveyed through spent fluid line 18 to waste 14. In case of presence of the ultrafiltration line 20, the spent fluid pump 19 may be controlled to balance the flow rate of dialysis fluid pump 17, such that fluid conveyed through line 15 represents the fluid ultrafiltered through the membrane, which may be collected in a separate vessel 22 or discharged to a waste. The embodiment of FIG. 3 presents an optional pre-dilution fluid line 23 connected to the blood withdrawal line 6: line 15 supplies replacement fluid from an infusion fluid container 24 connected at one end of the pre-dilution fluid line. Although in FIG. 3 the container 24 is shown as the source of infusion fluid, this should not be interpreted in a limitative manner: indeed, if the apparatus has an on line preparation section the infusion fluid may also come from said online preparation section. Note that alternatively to the pre-dilution fluid line the apparatus of FIG. 1 may include a post-dilution fluid line (not shown in FIG. 3) connected to the blood return line. Finally, as a further alternative (not shown in FIG. 3) the apparatus of FIG. 1 may include both a pre-dilution and a post infusion fluid line: in this case each infusion fluid line may be connected to a respective infusion fluid container or to a same infusion fluid container or to the fluid preparation section supplying online prepared fluid to the post and/or pre dilution lines. An infusion pump 25 operates on the infusion line 23 to regulate the flow rate $Q_{REP}$ through the infusion line. Note that in case of two infusion lines (pre-dilution and post-dilution) each infusion line may be provided with a respective infusion pump. Alternatively to what above described, infusion fluid (which can be in the form of a short bolus or in the form of a continuous flow) may come from a pipe directly connected to the fresh fluid line 15: in this case, the control unit may be configured to differentially drive pump 17 and a further pump located downstream the junction between said infusion pipe and line 15.

The hydraulic circuit 13 also comprises a bypass line 30 which puts into direct communication the fresh fluid line 15 with the spent fluid line 18 bypassing the second chamber 4 of the treatment unit 2. As shown in FIG. 2, in case of presence of an ultrafiltration line 20, the bypass line may be connected to the spent fluid line at a junction point 26 located downstream the branching off point 27 where the ultrafiltration line branches off the spent fluid line 18 (i.e. the branching off point 27 is closer to the outlet of the second chamber than the junction point 26). Furthermore, the hydraulic circuit comprises a fluid intercepting organ 31 configured for selectively switching fluid connection of the fresh fluid line to the second chamber 4 or to the bypass line 30, under control of control unit 10. In practice, the intercepting organ 31 may be a three way valve (see e.g. FIGS. 2 and 3) acting in correspondence the junction point 32 between the fresh fluid line 15 and the bypass line 30 and selectively connecting the fresh fluid line either with the bypass line (preventing fluid passage directed to the inlet of the second chamber) or with the second chamber inlet (preventing fluid passage through the bypass line). Alternatively, the fluid intercepting organ may comprise two valves 31a, 31b one operating on the bypass line 30 and one on the fresh fluid line 15 (FIG. 1): the two valves may be on/off valves controlled by control unit such that when one of the two valves is open the other is closed and vice versa. According to a further alternative, the fluid intercept organ may comprise a pump operating on the bypass line and a pump operating on the fresh fluid line. Of course, any other combination of pumps and valves capable of selectively conveying the treatment fluid either only through the bypass channel or only through the secondary chamber may be used.

Irrespective of the specific configuration of the fluid intercepting organ, the hydraulic circuit 13 is configured to operate in a normal mode, where the fresh fluid line 15 is connected and sends fluid to the inlet of a secondary chamber 4 of the treatment unit, and in an isolated ultrafiltration mode, where the fresh fluid line 15 does not convey fresh treatment liquid to the secondary chamber, but rather the fresh treatment liquid is sent directly to the spent fluid line 18, via bypass line 30, thereby bypassing the secondary chamber 4. The control unit is configured to control and command the switching of the hydraulic circuit 13 between the normal mode and the isolated ultrafiltration mode. In each one of the above described embodiments, sensors (for instance of the volumetric or of the mass type or of other nature) connected to the control unit 10 may be used in correspondence of one or more of the fluid lines 15, 18 and 23. These sensors are configured and positioned to measure or to allow calculation of the flow rate of the fluid flowing in each of the lines 15, 18 and—if present—in line 20, or to allow measure or calculation of the ultrafiltration flow rate $Q_{UF}$, i.e. the flow rate of fluid crossing the membrane 5. For instance in the example of FIG. 1, flow sensors 40, 41 located one on the fresh fluid line and one on the spent fluid line may be configured to allow detection or calculation of the difference between the flow rate $Q_{EFF}$ through the spent fluid line 18 and the flow rate $Q_{DIAL}$ through the fresh fluid line 15, this difference representing the ultrafiltration flow rate $Q_{UF}=Q_{EFF}-Q_{DIAL}$. Note that instead of two sensors one single differential sensor may be used which may be configured for directly measuring the difference between $Q_{EFF}$ and $Q_{DIAL}$.

In the case of FIG. 2, the ultrafiltration line 20 may be provided with a dedicated sensor such as a gravimetric sensor 42 configured for weighing vessel 22. The gravimetric sensors provides weight information $W_1$ relative to the amount of the fluid collected in the vessel 22 to the control unit 10 for the control unit to determine the actual ultrafiltration flow rate of fluid extracted from the patient's blood through the membrane 5.

In the case of FIG. 3, sensors 40, 41 or a single differential sensor may be used to determine $Q_{EFF}-Q_{DIAL}$. Given the presence of one or more infusion lines, such as line 23, sensors may be provided to determine or allow calculation by the control unit of the replacement fluid $Q_{REP}$ conveyed through the infusion line(s). In this case $Q_{UF}=Q_{EFF}-Q_{DIAL}$ also includes $Q_{REP}$ so that the real fluid flow rate ultrafiltered from the patient is given by $Q_{UF}-Q_{REP}$. Although in the above examples reference has been made to certain type of sensors, note that the sensors used for determining or allowing calculation of the flow rates through the various fluid lines or of the ultrafiltration flow rate may be of any convenient type: for instance in case the apparatus includes a container as source of fresh dialysis fluid and a container to collect waste, then scales may be used to detect the amount of fluid delivered or collected by each container and then inform the control unit accordingly. As a further alternative, systems based on volumetric control may be used where the fresh fluid line 15 and the spent fluid line 18 are connected to a balance chamber system assuring that—at each instant—the flow rate of liquid flowing through line 15 is identical to the flow rate of fluid through line 18: in this case only a sensor, e.g. a volumetric or mass or weigh sensor, on the ultrafiltration line may be necessary.

As already indicated the apparatus according to the invention makes use of at least one control unit 10 which may be connected to the sensors present in the apparatus and to the actuators, such as the blood pump, the ultrafiltration pump, the dialysis pump, the infusion pump(s) and the spent fluid pump. The control unit is also connected to user interface 12 and allows the user to enter a number of prescription parameters which may include a set value of the blood flow rate which is then used by the control unit 10, during treatment, to control the blood pump. The control unit, via user interface 12, may also receive other prescription parameters, e.g. a duration of the treatment time and a total fluid volume to be removed from the patient during the treatment session, for then setting appropriate set values to the various fluid pumps during treatment, as it will be described in further detail herein below. The control unit may comprise a digital processor (CPU) with memory (or memories), an analogical type circuit, or a combination of one or more digital processing units with one or more analogical processing circuits. In the present description and in the claims it is indicated that the control unit is "configured" or "programmed" to execute certain steps: this may be achieved in practice by any means which allow configuring or programming the control unit. For instance, in case of a control unit comprising one or more CPUs, one or more programs are stored in an appropriate memory: the program or programs containing instructions which, when executed by the control unit, cause the control unit to execute the steps described and/or claimed in connection with the control unit. Alternatively, if the control unit is of an analogical type, then the circuitry of the control unit is designed to include circuitry configured, in use, to process electric signals such as to execute the control unit steps herein disclosed.

In accordance with aspects of the invention, the control unit 10 is configured for executing the steps and procedures described below. In below description reference is made to a control unit operating on an apparatus configured as in FIG. 1 or in FIG. 2 (hemodialysis apparatus). Of course the control unit 10 may operate as described below also in an apparatus of the type of FIG. 3 (hemodiafiltration apparatus), account being taken for the presence of one or more infusion lines and corresponding replacement fluid flow rates which, as also explained herein above, affect the relationship between ultrafiltration rate and weight loss rate.

Figure 4:
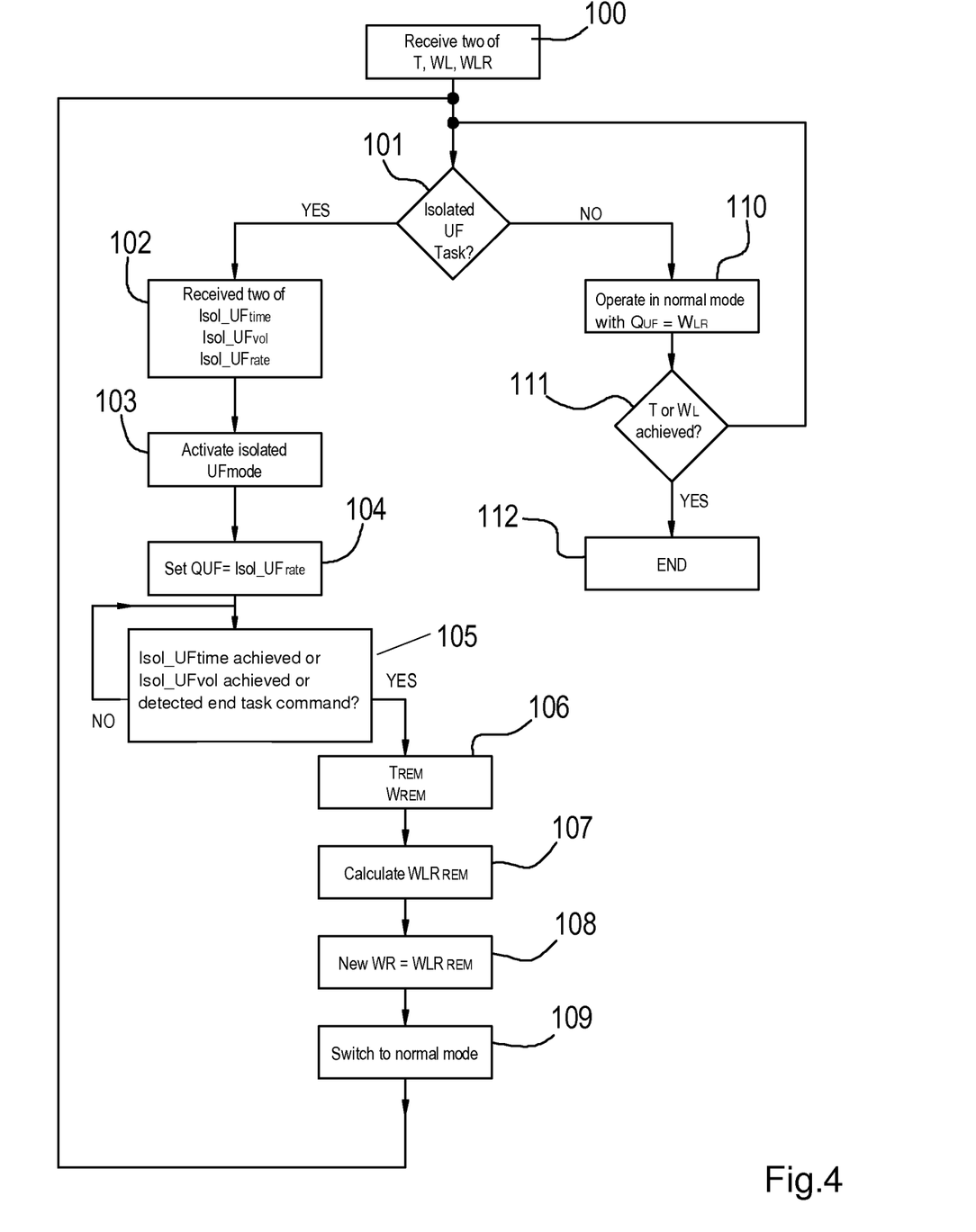
FIG. 4 is a schematic flowchart of steps for setting a blood treatment apparatus according to one aspect of the invention. The shown steps may executed by the control unit of the blood treatment apparatus.

Referring to the flowchart of FIG. 4 which schematically shows the steps the control unit is configured to execute, it should be noted that the control unit is configured for receiving at least two general setup values selected among the following three parameters (step 100):
 a) a prescription value for a total treatment time T during which the patient is to be submitted to blood treatment,
 b) a prescription value for a total patient fluid WL removal to be achieved by the end of total treatment time,
 c) a prescription value for an average patient fluid removal rate WLR to be kept across total treatment time.

In apparatus for chronic care as the ones herein described the control unit 10, before start of the treatment, is configured to receive values for the total treatment time T and for the total fluid removal WL (which can be expressed as a volume loss or as a weight loss) to be achieved by the end of treatment time T. It is however understood that the initial setup of the apparatus may also be made by configuring the control unit to receive any two of the three general setup parameters mentioned above, as the third may in any case be calculated based on the other two. The general setup parameters may be entered to the control unit via user interface 12, which may be a touch screen user interface capable of displaying indicia for allowing entry of said parameters, or may be a user interface provided with a normal screen and knobs or hardware keys for entering said parameters, or a combination of a touch screen+hardware keys user interface or a user interface of other nature. Of course the general setup parameters and any other parameter which should be received by the control unit may be entered in any other convenient manner, e.g. by way of non limiting example by remote transmission, via voice entry, or using appropriate readers.

The control unit 10 is further configured for executing an isolated ultrafiltration task: for example the control unit may be configured to execute said task once or a plurality of times at distinct and timely spaced time intervals during treatment time. The activation of the isolated ultrafiltration task may be made immediately at treatment start if the control unit receives a request (step 101) for initiating an isolated UF procedure (this request may be generated if the user before treatment start has programmed the appropriate parameters for execution of the isolated ultrafiltration) or during treatment if the control unit detects an activation command (step 101) entered via a data entry unit (part of the user interface 12) connected to the control unit, requesting execution of the isolated ultrafiltration task. Furthermore, the activation of the isolated ultrafiltration mode may be made automatically by the control unit at prefixed instants during treatment by automatic generation of a request directed to the control unit: in this case either the user is requested to enter values of isolated ultrafiltration parameters or the control unit uses prestored values of said parameters.

The isolated ultrafiltration task comprises the steps of receiving values of at least two isolated ultrafiltration parameters (step 102) selected in the group comprising:
 1) an isolated ultrafiltration time, $Isol\_UF_{Time}$, which is a time interval during which the apparatus is requested to operate in said isolated ultrafiltration mode,
 2) an isolated ultrafiltration volume, $Isol\_UF_{Vol}$, which is volume of fluid to be removed from the patient while the apparatus is requested to operate in said isolated ultrafiltration mode,
 3) an isolated ultrafiltration rate, $Isol\_UF_{Rate}$, which is rate of fluid removal from the patient while the apparatus is requested to operate in said isolated ultrafiltration mode.

For instance the control unit may be configured to receive the isolated ultrafiltration time, $Isol\_UF_{Time}$, and the isolated ultrafiltration volume, $Isol\_UF_{Vol}$, and to calculate the $Isol\_UF_{Rate}$ as:

$$Isol\_UF_{Rate}=(Isol\_UF_{Vol})/(Isol\_UF_{Time}).$$

The control unit is configured to then activate the isolated ultrafiltration mode (step 103) by controlling hydraulic circuit 13, namely acting on the fluid intercepting organ 31, and cause the hydraulic circuit 13 to switch into the isolated ultrafiltration mode. When the hydraulic circuit has been switched to isolated ultrafiltration mode, the control unit controls at least one ultrafiltration actuator of the hydraulic circuit (step 104) based on the values of the isolated ultrafiltration time and the isolated ultrafiltration volume and, in detail, based on the ratio:

$$Isol\_UF_{Rate}=(Isol\_UF_{Vol})/(Isol\_UF_{Time}).$$

For instance, with reference to FIG. 1, the at least one ultrafiltration actuator may include fluid pumps 17, 19 which are differentially controlled to pull the desired ultrafiltration through the membrane 5. In the example of FIG. 2 the ultrafiltration actuator includes pump 21 which is driven such as to achieve an ultrafiltration flow rate $Q_{UF}=Isol\_UF_{Rate}$, while pumps 17 and 19 may be driven such as to be perfectly balanced.

The hydraulic circuit is kept by control unit 10 in isolated ultrafiltration mode until achievement of the set target(s), namely until collection of the isolated ultrafiltration volume $Isol\_UF_{Vol}$ or until elapse of the ultrafiltration time $Isol\_UF_{Time}$ as shown in FIG. 4 by loop 105. In practice the control unit checks achievement of the target(s) and then either automatically or after user confirmation returns the hydraulic circuit into normal mode also taking the further steps described below. In detail, once reached the isolated ultrafiltration target(s), the isolated ultrafiltration task comprises calculating (step 106), based e.g. on the set values the two isolated ultrafiltration parameters $Isol\_UF_{Vol}$ and $Isol\_UF_{Time}$ a remaining treatment time $T_{REM}$ which is the treatment time during which the patient shall be submitted to blood treatment with the apparatus operating in normal mode after operation in isolated ultrafiltration mode, and a remaining patient fluid removal $WL_{REM}$ which is a volume of fluid to be extracted from the patient with the apparatus operating in normal mode after operation in isolated ultrafiltration mode. In accordance with an embodiment, the remaining treatment time is calculated as difference between the total treatment time T and the isolated ultrafiltration time $Isol\_UF_{Time}$ and the remaining patient fluid removal as difference from the total patient fluid WL and the isolated ultrafiltration volume $Isol\_UF_{Vol}$:

$$T_{REM}=T-(Isol\_UF_{Time})$$

$$WL_{REM}=WL-(Isol\_UF_{Vol})$$

Alternatively, or additionally, the control unit may be configured to calculate a remaining patient fluid removal rate $WLR_{REM}$ (step 107) based on said isolated ultrafiltration rate or on said $T_{REM}$ and $WL_{REM}$. The remaining patient fluid removal rate is the rate of fluid to be extracted from the patient with the apparatus operating in normal mode after operation in isolated ultrafiltration mode, such as to achieve the prescribed total fluid removal WL by the end of the total treatment time T. Thus, before returning to normal mode the control unit is configured (step 108) to set as new WLR the calculated $WLR_{REM}$.

In practice, during execution of the isolated ultrafiltration task, the control unit causes the hydraulic circuit to operate in isolated ultrafiltration mode for the duration of said isolated ultrafiltration time, or until withdrawal from a patient of said isolated ultrafiltration volume (steps 104 and 105); then control unit 10 causes the hydraulic circuit 13 to switch from isolated ultrafiltration mode to normal mode (step 109): in normal mode the ultrafiltration rate is controlled based on the value of the remaining patient fluid removal rate ($Q_{UF}$=WLR=$WLR_{REM}$) so that T and WL will be achieved at the end of treatment (step 110). The ultrafiltration rate is controlled by the control unit acting on the at least one actuator: as already discussed in case of the example of FIG. 1 the at least one ultrafiltration actuator includes fluid pumps 17, 19 which are differentially controlled to pull the desired ultrafiltration $Q_{UF}$=WLR=$WLR_{REM}$ through the membrane 5, while in the example of FIG. 2 the ultrafiltration actuator includes pump 21 which is driven such as to achieve $Q_{UF}$=WLR=$WLR_{REM}$, while pumps 17 and 19 may be driven such as to be perfectly balanced. The control unit periodically or continuously check achievement of the prescription value for the total treatment time T or of the prescription value for the total patient fluid removal WL (step 111) and in the affirmative controls the apparatus to stop the treatment (step 112), e.g. by stopping the blood pump and informing the user, e.g. via user interface 12, about treatment end and need to initiate the end treatment sequence leading to separation of the patient from the apparatus. As indicated by loop 113 in the schematic flowchart of FIG. 4, the control unit continues to operate in normal mode until when a new request for execution of an isolated UF task is received by the control unit (step 101).

Figure 5:
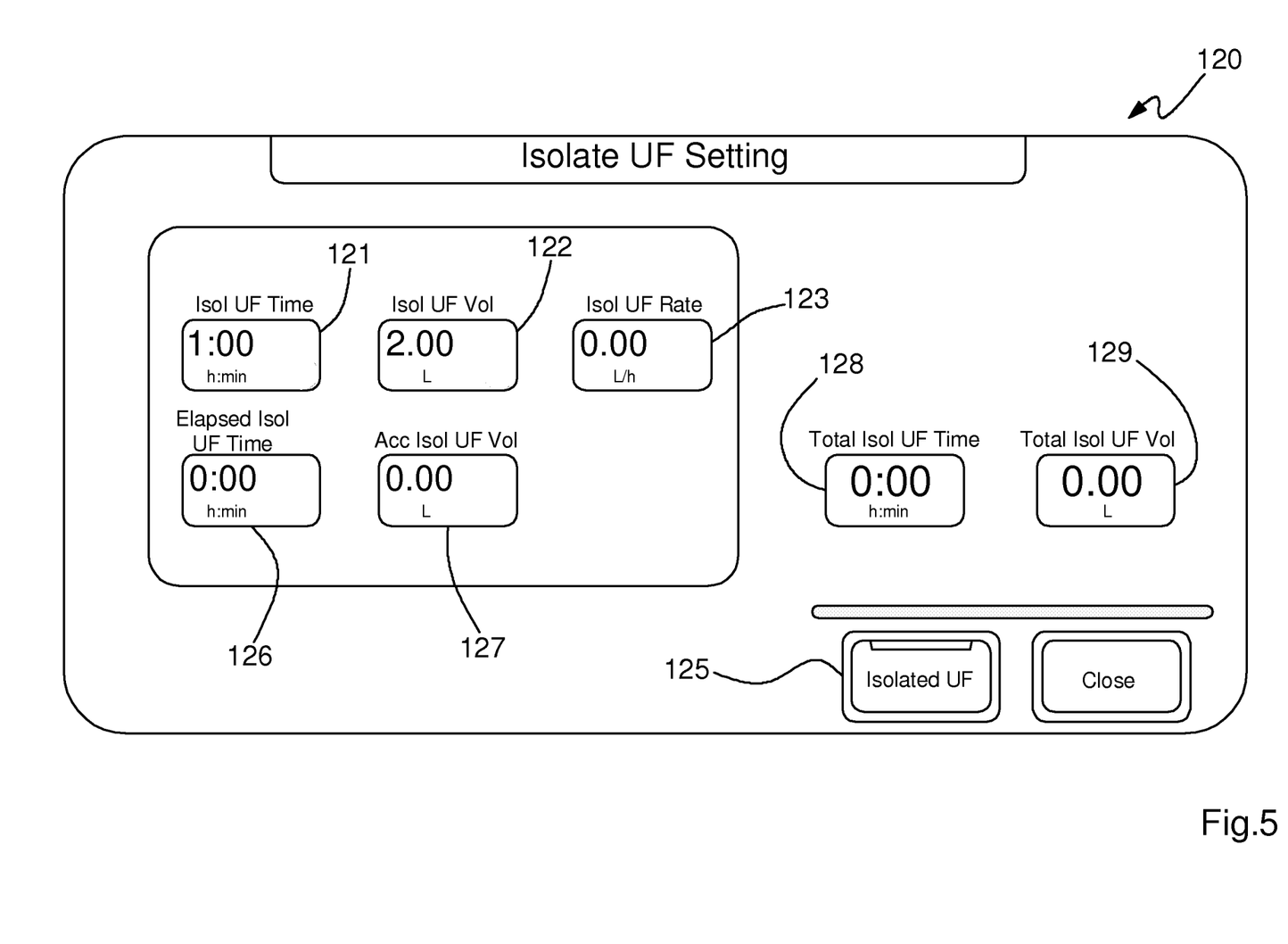
FIGS. 5-7 show reproductions of a user interface display, e.g. in the form of a touch screen, adapted for setting the parameters necessary for execution of the ultrafiltration task according to aspects of the invention.
Figure 6:
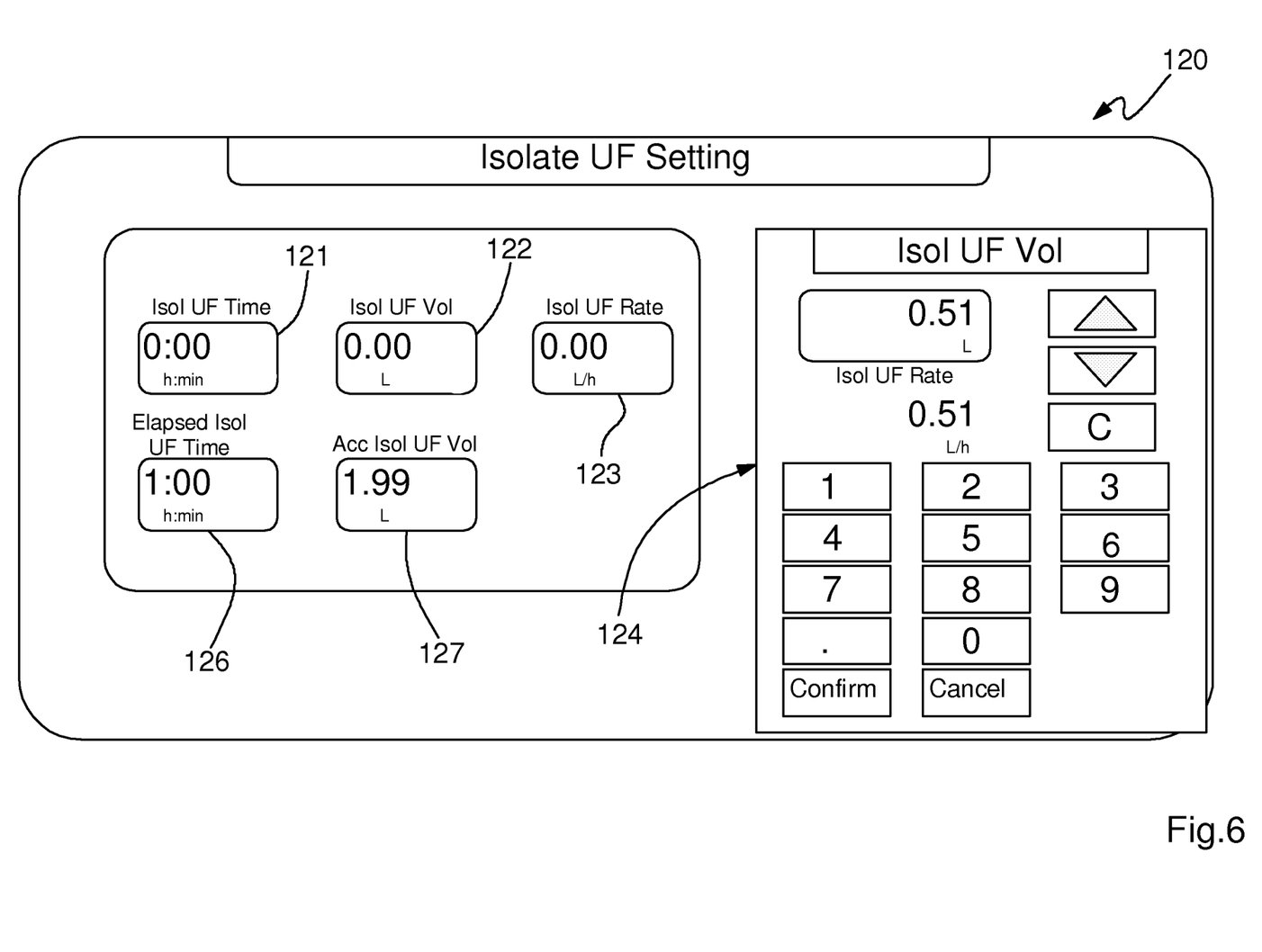
Figure 7:
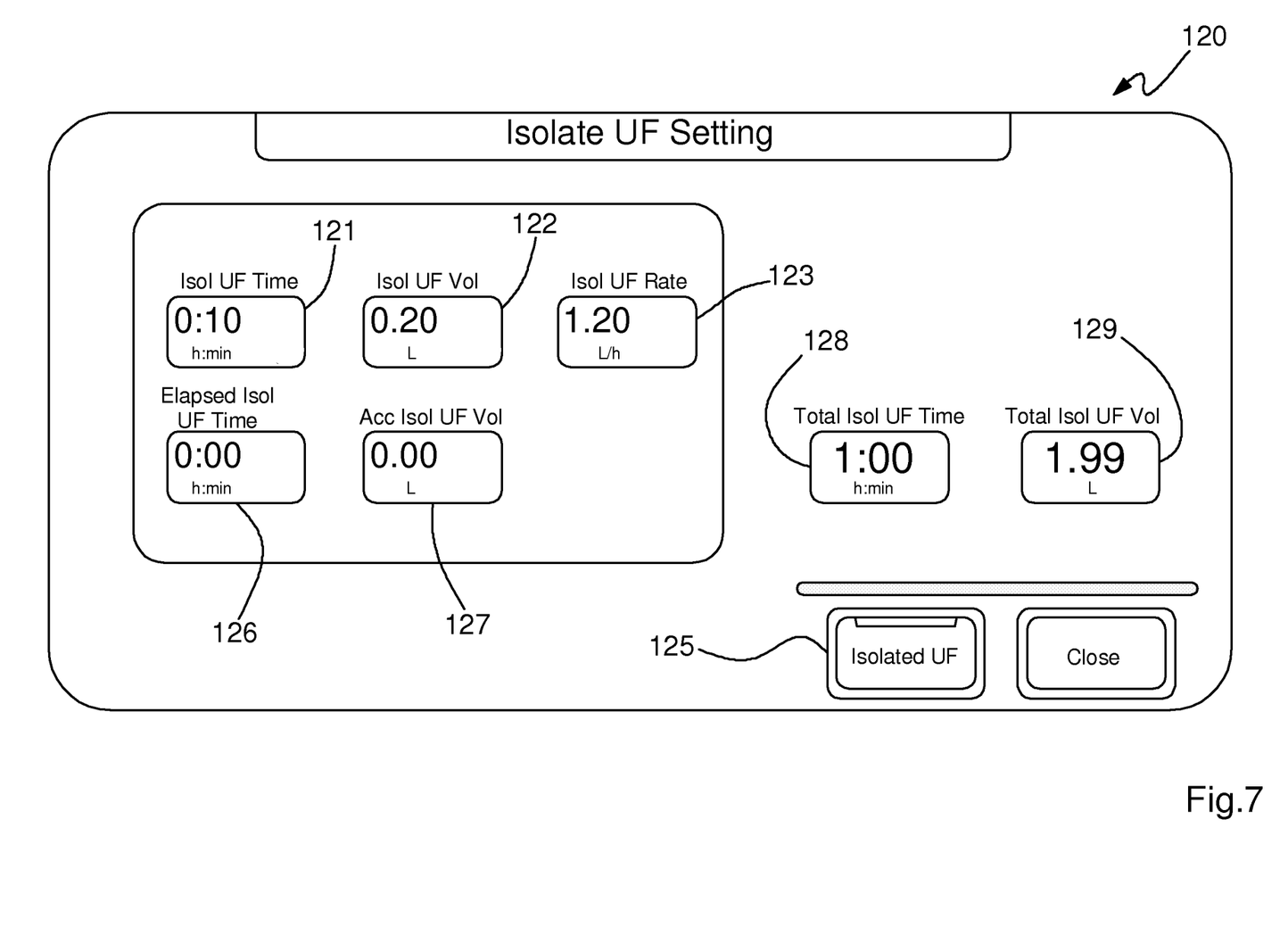

With reference to FIGS. 5-7, an example of a user interface 12 and of steps for setting the parameters necessary for execution of the ultrafiltration tasks is described.

As shown in FIGS. 5-7 the user interface comprises a touch screen. The control unit is configured to display on the touch screen at least one screen portion 120 comprising:
- a first selectable indicium 121, which in FIG. 5 is in the form of a touch sensitive button, for entering the isolated ultrafiltration time, and
- a second selectable indicium 122, which in FIG. 5 is in the form of a touch sensitive button, for entering the isolated ultrafiltration volume.

As it can be seen in FIG. 7, the control unit is configured to calculate and display the isolated ultrafiltration rate derivable from the entered values of isolated ultrafiltration time and volume. The isolated ultrafiltration rate is displayed for example in a dedicated area 123. As shown in FIG. 6, entry of the isolated ultrafiltration parameter may be made by selecting the corresponding indicium which causes the control unit to display a data entry tool 124 (such as a keypad) for entering the desired value of each parameter.

The control unit may also display a confirmation indicium 125 for the user to send the request of activation of the isolated ultrafiltration task.

Note that alternatively to what has been described, the value of the isolated ultrafiltration time or the value of the isolated ultrafiltration value or the value of the isolated ultrafiltration rate may be prefixed value(s) pre-stored in a memory connected to the control unit, such that the user may only need to activate the ultrafiltration task with no need of further actions. In other words, isolated ultrafiltration parameters may be prestored in a memory connected to the control unit. This latter may be configured to detect an activation command and run an isolated ultrafiltration task based on the pre-stored isolated ultrafiltration parameters and then automatically return to normal mode and prosecute the treatment.

As shown in FIGS. 5-7, the control unit 10 may also be configured to calculate:
- an accumulated isolated ultrafiltration volume which is the isolated ultrafiltration volume removed from the patient during the isolated ultrafiltration task under execution (area 126);
- an elapsed isolated ultrafiltration time which is the time interval since initiation of the isolated ultrafiltration task under execution (area 127);
- a total isolated ultrafiltration volume which is the sum of the isolated ultrafiltration volumes removed from the patient after execution of a plurality of completed isolated ultrafiltration tasks (area 128); the control unit may be programmed to update the total isolated ultrafiltration volume only after activation of a new isolated ultrafiltration task;
- a total isolated ultrafiltration time which is the sum of the time intervals of execution of a plurality of completed isolated ultrafiltration tasks (area 129); the control unit may be programmed to update the total isolated ultrafiltration time only after activation of a new isolated ultrafiltration task.

For instance, FIG. 5 refers to a stage of setting the prescription values for the isolated UF time and Isolated UF volume for a first ultrafiltration task to be executed: no isolated ultrafiltration tasks have been initiated yet so the control unit 10 displays 0 (zero) minutes and 0 (zero) liters in areas 126 and 127 respectively as the values for elapsed isolated ultrafiltration time and accumulated isolated ultrafiltration volume. Analogously, as no previous isolated ultrafiltration tasks in the same treatment time T had been completed, the control unit 10 displays 0 (zero) minutes and 0 (zero) liters in areas 128 and 129 respectively as the values for the total isolated ultrafiltration time and volume.

FIG. 6, refers to a stage of configuring a new isolated UF session after completion of one isolated UF session:

basically after completion of one isolated UF session, the displays in areas 121 and 122 are reset to 0 (zero) and the user is offered the possibility to enter new values for the isolated UF time and volume via entry tool (e.g. keypad) 124. In this case, areas 126 and 127 show the elapsed time and accumulated volume of the previous isolated UF session. FIG. 6 shows a situation where the new isolated UF session has not been activated yet and with the data entry tool overlapping the areas 128 and 129. Note that after data entry tool disappears and until the new ultrafiltration session is activated, the control unit 10 will display 0 (zero) minutes and 0 (zero) liters in areas 128 and 129 respectively as the values of total isolated ultrafiltration time and volume.

FIG. 7, refers to a stage after activation of a new isolated UF session and after completion of one isolated UF session. In this case areas 126 and 127 displays 0 (zero) minutes and 0 (zero) liters in areas 126 and 127 respectively as the values of elapsed isolated ultrafiltration time and accumulated isolated ultrafiltration volume because the new isolated ultrafiltration task has just been initiated. Vice versa, as the new isolated UF session has been activated, the control unit 10 displays the minutes and liters in areas 128 and 129 respectively corresponding to the values of total isolated ultrafiltration time and volume cumulated across the previous isolated ultrafiltration session.

It should also be noted that the control unit may be configured to run a safety check comprising comparing the received values of the isolated ultrafiltration parameters against respective safety thresholds and preventing the hydraulic circuit to operate in isolated ultrafiltration mode if the safety check is not positively passed. For instance, the control unit may be configured to compare the isolated ultrafiltration rate against a maximum threshold and prevent the user to set isolated ultrafiltration parameters causing the isolated ultrafiltration rate to pass the respective threshold. Furthermore, the control unit may calculate the isolated ultrafiltration time and the isolated ultrafiltration volume with the total treatment time or with the total fluid removal and prevent conflicting settings.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An extracorporeal blood treatment apparatus comprising:
a blood treatment unit having a primary chamber configured to receive blood of a patient to be treated, and a secondary chamber separated from the primary chamber by a semi-permeable membrane;
an hydraulic circuit having a fresh fluid line configured to connect to an inlet of the secondary chamber, and a spent fluid line configured to connect to an outlet of said secondary chamber and configured to remove spent liquid from the secondary chamber and convey it to at least one waste,
a control unit operably connected to the hydraulic circuit and configured to control the hydraulic circuit to selectively operate in a normal mode, where the fresh fluid line is connected to the inlet of the secondary chamber of the treatment unit and conveys fresh treatment liquid to the secondary chamber, and wherein the control unit is further configured to control the hydraulic circuit to selectively operate in an isolated ultrafiltration mode, where the fresh fluid line does not convey fresh treatment liquid to the secondary chamber,
the control unit further configured to execute a setup phase before starting treatment, the setup phase comprising:
receiving at least two general setup values selected from:
a prescription value for a total treatment time during which the patient is to be submitted to blood treatment,
a prescription value for a total patient fluid removal to be achieved by the end of total treatment time,
a prescription value for an average patient fluid removal rate to be kept across total treatment time;
receiving instructions to execute a selected plurality of isolated ultrafiltration tasks during the total treatment time, wherein the control unit is configured to:
receive, for each isolated ultrafiltration task of the plurality of isolated ultrafiltration tasks, values of at least two isolated ultrafiltration parameters selected from:
an isolated ultrafiltration time, which is a time interval during which the apparatus is requested to operate in said isolated ultrafiltration mode,
an isolated ultrafiltration volume, which is a volume of fluid to be removed from the patient while the apparatus is requested to operate in said isolated ultrafiltration mode,
an isolated ultrafiltration rate which is a rate of fluid removal from the patient while the apparatus is requested to operate in said isolated ultrafiltration mode;
determining, during the setup phase, at least one of:
a remaining treatment time based on said isolated ultrafiltration time of each isolated ultrafiltration task of the plurality of isolated ultrafiltration tasks, the remaining treatment time being a treatment time during which the patient shall be submitted to blood treatment with the apparatus operating in normal mode after operation in isolated ultrafiltration mode,
a remaining patient fluid removal based on said isolated ultrafiltration volume of each isolated ultrafiltration task of the plurality of isolated ultrafiltration tasks, the remaining patient fluid removal being a volume of fluid to be extracted from the patient with the apparatus operating in normal mode after operation in isolated ultrafiltration mode,
a remaining patient fluid removal rate based on said isolated ultrafiltration rate of each isolated ultrafiltration task of the plurality of isolated ultrafiltration tasks, the remaining patient fluid removal rate being a rate of fluid to be extracted from the patient with the apparatus operating in normal mode after operation in isolated ultrafiltration mode;
wherein the control unit is configured to control the hydraulic circuit to operate in isolated ultrafiltration mode during the total treatment time corresponding to the selected plurality of isolated ultrafiltration tasks and based on the values of at the least two isolated ultrafiltration parameters received for each isolated ultrafiltration task of the plurality of isolated ultrafiltration tasks;
wherein, when the hydraulic circuit is operating in the isolated ultrafiltration mode, the control unit is further configured to control the hydraulic circuit to switch from operating in the isolated ultrafiltration mode to the normal mode upon the first of:
passage of all of said isolated ultrafiltration time;
withdrawal from a patient of said isolated ultrafiltration volume; or
receipt of a command from a user interface connected to the control unit indicating to end the isolated ultrafiltration mode;
and wherein, when operating the hydraulic circuit in the normal mode after operating in the isolated ultrafiltration mode, the control unit is configured to operate the hydraulic circuit in the normal mode based on the values of two of: the remaining treatment time, the remaining patient fluid removal, and the remaining patient fluid removal rate determined during the setup phase for each isolated ultrafiltration task of the plurality of isolated ultrafiltration tasks.

2. An apparatus according to claim 1, wherein during the setup phase, the control unit is configured to:
receive, as two general setup values, the prescription value for the total treatment time and the prescription value for the total patient fluid removal;
receive, as two isolated ultrafiltration parameters for each isolated ultrafiltration task of the plurality of isolated ultrafiltration tasks, the isolated ultrafiltration time and the isolated ultrafiltration volume;
determine the remaining treatment time at least based on the isolated ultrafiltration time of each isolated ultrafiltration task of each of the plurality of isolated ultrafiltration tasks and on said prescription value for a total treatment time;
determine the remaining patient fluid removal based on the isolated ultrafiltration volume of each isolated ultrafiltration task of the plurality of isolated ultrafiltration tasks and on the prescription value for a total patient fluid removal;
wherein causing the hydraulic circuit to operate in the isolated ultrafiltration mode for each isolated ultrafiltration task of the plurality of isolated ultrafiltration tasks comprises controlling at least one ultrafiltration actuator of the hydraulic circuit based on the isolated ultrafiltration time and the isolated ultrafiltration volume for each isolated ultrafiltration task of the plurality of isolated ultrafiltration tasks;
and wherein causing the hydraulic circuit to operate in the normal mode after operating the hydraulic circuit in isolated ultrafiltration mode for each isolated ultrafiltration task of the plurality of isolated ultrafiltration tasks comprises controlling at least one ultrafiltration actuator of the hydraulic circuit based on the values of the remaining treatment time and the remaining patient fluid removal.

3. An apparatus according to claim 2, wherein the control unit is configured to:
calculate the value of the remaining patient fluid removal rate based on the following equation: remaining patient fluid removal rate=(remaining patient fluid removal)/(remaining treatment time), and
control at least one ultrafiltration actuator of the hydraulic circuit in the normal mode based on the calculated value of the remaining patient fluid removal rate.

4. An apparatus according to claim 1, wherein receiving the value of the isolated ultrafiltration time comprises either receiving a prefixed value pre-stored in a memory connected to the control unit, or receiving an entered value for the isolated ultrafiltration time via a data entry unit connected to the control unit.

5. An apparatus according to claim 1, wherein receiving the value of the isolated ultrafiltration volume comprises either receiving a prefixed value pre-stored in a memory connected to the control unit, or receiving an entered value for the isolated ultrafiltration volume via a data entry unit connected to the control unit.

6. An apparatus according to claim 1, wherein receiving the value of the isolated ultrafiltration rate comprises either receiving a prefixed value pre-stored in a memory connected to the control unit, or receiving an entered value for the isolated ultrafiltration rate via a data entry unit connected to the control unit.

7. An apparatus according to claim 1, wherein the control unit is configured to execute each isolated ultrafiltration task of the plurality of isolated ultrafiltration tasks with each isolated ultrafiltration task of the plurality of isolated ultrafiltration tasks being executed at distinct and timely spaced time intervals during said total treatment time.

8. An apparatus according to claim 1, wherein the control unit is configured to start a treatment controlling the hydraulic circuit in said normal mode, detect an activation command entered via a data entry unit connected to the control unit, and request execution of the isolated ultrafiltration task in response to detection of said activation command.

9. An apparatus according to claim 1, wherein the control unit is configured to calculate at least one of:
an accumulated isolated ultrafiltration volume which is the isolated ultrafiltration volume removed from the patient during the ultrafiltration task under execution;
an elapsed isolated ultrafiltration time which is the time interval since initiation of the ultrafiltration task under execution; and
an accumulated isolated ultrafiltration volume which is the isolated ultrafiltration volume removed from the patient during the ultrafiltration task under execution and an elapsed isolated ultrafiltration time which is the time interval since initiation of the ultrafiltration task under execution.

10. An apparatus according to claim 1, wherein the control unit is configured to calculate at least one of:
a total isolated ultrafiltration volume which is the sum of the isolated ultrafiltration volumes removed from the patient after execution of a plurality of ultrafiltration tasks, and
a total isolated ultrafiltration time which is the sum of the time intervals of execution of a plurality of ultrafiltration tasks.

11. An apparatus according to claim 1, wherein the control unit is further configured to conduct a safety check comprising comparing the received values of the isolated ultrafiltration parameters against at least one respective safety threshold and preventing operation of the hydraulic circuit in the isolated ultrafiltration mode if the safety check is not positively passed.

12. An apparatus according to claim 1, wherein the hydraulic circuit comprises at least one ultrafiltration actuator acting on the spent fluid line or on an ultrafiltration line branching off the spent fluid line, and wherein the control unit is configured to:
drive said at least one ultrafiltration actuator, and
cause, during at least one isolated ultrafiltration task of the plurality of isolated ultrafiltration tasks, said at least one ultrafiltration actuator to extract fluid from the secondary chamber.

13. An extracorporeal blood treatment apparatus comprising:
a blood treatment unit having a primary chamber configured to receive blood of a patient to be treated, and a secondary chamber separated from the primary chamber by a semi-permeable membrane;
a hydraulic circuit having a fresh fluid line configured to connect to an inlet of the secondary chamber, a spent fluid line configured to connect to an outlet of said secondary chamber and configured to remove spent liquid from the secondary chamber and convey it to at least one waste,
a control unit operably connected to the hydraulic circuit and configured to control the hydraulic circuit to selectively operate in a normal mode, where the fresh fluid line is connected to the inlet of the secondary chamber of the treatment unit and conveys fresh treatment liquid to the secondary chamber, and wherein the control unit is further configured to control the hydraulic circuit to selectively operate in an isolated ultrafiltration mode, where the fresh fluid line does not convey fresh treatment liquid to the secondary chamber, the control unit further configured to execute a setup phase before starting treatment, the setup phase comprising:

receiving at least two general setup values selected from:
- a prescription value for a total treatment time during which the patient is to be submitted to blood treatment,
- a prescription value for a total patient fluid removal to be achieved by the end of total treatment time,
- a prescription value for an average patient fluid removal rate to be kept across total treatment time;

receiving instructions to execute one or more isolated ultrafiltration tasks during the total treatment time, wherein the control unit is configured to:
- receive, for each isolated ultrafiltration task of the one or more isolated ultrafiltration tasks, values of at least two isolated ultrafiltration parameters selected from:
  - an isolated ultrafiltration time, which is a time interval during which the apparatus is requested to operate in said isolated ultrafiltration mode,
  - an isolated ultrafiltration volume, which is a volume of fluid to be removed from the patient while the apparatus is requested to operate in said isolated ultrafiltration mode,
  - an isolated ultrafiltration rate which is a rate of fluid removal from the patient while the apparatus is requested to operate in said isolated ultrafiltration mode;
- determine, during the setup phase, at least one of:
  - a remaining treatment time based on said isolated ultrafiltration time of each isolated ultrafiltration task of the one or more isolated ultrafiltration tasks, the remaining treatment time being a treatment time during which the patient shall be submitted to blood treatment with the apparatus operating in normal mode after operation in isolated ultrafiltration mode,
  - a remaining patient fluid removal based on said isolated ultrafiltration volume of each isolated ultrafiltration task of the one or more isolated ultrafiltration tasks, the remaining patient fluid removal being a volume of fluid to be extracted from the patient with the apparatus operating in normal mode after operation in isolated ultrafiltration mode,
  - a remaining patient fluid removal rate based on said isolated ultrafiltration rate of each isolated ultrafiltration task of the one or more isolated ultrafiltration tasks, the remaining patient fluid removal rate being a rate of fluid to be extracted from the patient with the apparatus operating in normal mode after operation in isolated ultrafiltration mode;

wherein the control unit is configured to control the hydraulic circuit to operate in isolated ultrafiltration mode during the total treatment time corresponding to the one or more isolated ultrafiltration tasks and based on the values of at the least two isolated ultrafiltration parameters received for each isolated ultrafiltration task of the one or more isolated ultrafiltration tasks;

wherein, when the hydraulic circuit is operating in the isolated ultrafiltration mode, the control unit is further configured to control the hydraulic circuit to switch from operating in the isolated ultrafiltration mode to the normal mode upon the first of:
- passage of all of said isolated ultrafiltration time;
- withdrawal from a patient of said isolated ultrafiltration volume; or
- receipt of a command from a user interface connected to the control unit indicating to end the isolated ultrafiltration mode;

and wherein, when operating the hydraulic circuit in the normal mode after operating in the isolated ultrafiltration mode, the control unit is configured to operate the hydraulic circuit in the normal mode based on the values of two of: the remaining treatment time, the remaining patient fluid removal, and the remaining patient fluid removal rate determined during the setup phase for each isolated ultrafiltration task of the one or more isolated ultrafiltration tasks.

14. An apparatus according to claim 13, wherein during the setup phase, the control unit is configured to:
- receive, as two general setup values, the prescription value for the total treatment time and the prescription value for the total patient fluid removal;
- receive, as two isolated ultrafiltration parameters for each isolated ultrafiltration task of the one or more isolated ultrafiltration tasks, the isolated ultrafiltration time and the isolated ultrafiltration volume;
- determine the remaining treatment time at least based on the isolated ultrafiltration time of each isolated ultrafiltration task of each of the one or more isolated ultrafiltration tasks and on said prescription value for a total treatment time;
- determine the remaining patient fluid removal based on the isolated ultrafiltration volume of each isolated ultrafiltration task of the one or more isolated ultrafiltration tasks and on the prescription value for a total patient fluid removal;
- wherein causing the hydraulic circuit to operate in the isolated ultrafiltration mode for each isolated ultrafiltration task of the one or more isolated ultrafiltration tasks comprises controlling at least one ultrafiltration actuator of the hydraulic circuit based on the isolated ultrafiltration time and the isolated ultrafiltration volume for each isolated ultrafiltration task of the one or more isolated ultrafiltration tasks;
- and wherein causing the hydraulic circuit to operate in the normal mode after operating the hydraulic circuit in isolated ultrafiltration mode for each isolated ultrafiltration task of the one or more isolated ultrafiltration tasks comprises controlling at least one ultrafiltration actuator of the hydraulic circuit based on the values of the remaining treatment time and the remaining patient fluid removal.

15. An apparatus according to claim 14, wherein the control unit is configured to:

calculate the value of the remaining patient fluid removal rate based on the following equation: remaining patient fluid removal rate=(remaining patient fluid removal)/(remaining treatment time), and control at least one ultrafiltration actuator of the hydraulic circuit in the normal mode based on the calculated value of the remaining patient fluid removal rate.

16. An apparatus according to claim 13, wherein receiving the value of the isolated ultrafiltration volume comprises either receiving a prefixed value pre-stored in a memory connected to the control unit, or receiving an entered value for the isolated ultrafiltration volume via a data entry unit connected to the control unit.

17. An apparatus according to claim 13, wherein the control unit is configured to execute each isolated ultrafiltration task of the one or more isolated ultrafiltration tasks with each isolated ultrafiltration task of the one or more isolated ultrafiltration tasks being executed at distinct and timely spaced time intervals during said total treatment time.

18. An apparatus according to claim 13, wherein the control unit is configured to calculate:
- an accumulated isolated ultrafiltration volume which is the isolated ultrafiltration volume removed from the patient during the ultrafiltration task under execution;
- an elapsed isolated ultrafiltration time which is the time interval since initiation of the ultrafiltration task under execution; or
- an accumulated isolated ultrafiltration volume which is the isolated ultrafiltration volume removed from the patient during the ultrafiltration task under execution and an elapsed isolated ultrafiltration time which is the time interval since initiation of the ultrafiltration task under execution.

19. An apparatus according to claim 13, wherein the control unit is configured to calculate at least one of:
- a total isolated ultrafiltration volume which is the sum of the isolated ultrafiltration volumes removed from the patient after execution of the one or more isolated ultrafiltration tasks, and
- a total isolated ultrafiltration time which is the sum of the time intervals of execution of the one or more isolated ultrafiltration tasks.

20. An apparatus according to claim 13, wherein the control unit is further configured to conduct a safety check comprising comparing the received values of the isolated ultrafiltration parameters against at least one respective safety threshold and preventing operation of the hydraulic circuit in the isolated ultrafiltration mode if the safety check is not positively passed.

\* \* \* \* \*